US011812931B2

(12) United States Patent
Kurihara et al.

(10) Patent No.: US 11,812,931 B2
(45) Date of Patent: Nov. 14, 2023

(54) OVERTUBE SYSTEM AND OPERATION METHOD OF THE SAME

(71) Applicant: OLYMPUS CORPORATION, Tokyo (JP)

(72) Inventors: Kyohei Kurihara, Tokyo (JP); Kosuke Kishi, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 610 days.

(21) Appl. No.: 17/102,673

(22) Filed: Nov. 24, 2020

(65) Prior Publication Data

US 2021/0076907 A1 Mar. 18, 2021

Related U.S. Application Data

(63) Continuation of application No. PCT/JP2018/021991, filed on Jun. 8, 2018.

(51) Int. Cl.
*A61B 1/00* (2006.01)
*A61M 25/10* (2013.01)

(52) U.S. Cl.
CPC ........ *A61B 1/0016* (2013.01); *A61B 1/00006* (2013.01); *A61B 1/00082* (2013.01); *A61B 1/00135* (2013.01); *A61B 1/00154* (2013.01); *A61M 25/1011* (2013.01)

(58) Field of Classification Search
None
See application file for complete search history.

(56) References Cited

U.S. PATENT DOCUMENTS

| 2008/0091063 A1* | 4/2008 | Terliuc ............... A61B 1/31 600/116 |
| 2008/0269559 A1* | 10/2008 | Miyamoto ......... A61B 1/00148 600/116 |
| 2010/0022825 A1 | 1/2010 | Yoshie |
| 2014/0094833 A1 | 4/2014 | Malhi |

(Continued)

FOREIGN PATENT DOCUMENTS

| EP | 1943938 A1 | 7/2008 |
| EP | 3263063 A1 | 1/2018 |

(Continued)

OTHER PUBLICATIONS

International Search Report dated Aug. 14, 2018 issued in PCT/JP2018/021991.

*Primary Examiner* — John P Leubecker
(74) *Attorney, Agent, or Firm* — Scully, Scott, Murphy & Presser, P.C.

(57) ABSTRACT

An overtube system configured to introduce an endoscope into a body, includes a tubular main body formed to be insertable for the endoscope; a balloon attached to an outer circumferential surface of the main body; a driver configured to inflate and deflate the balloon; and a controller configured to control the driver, wherein the controller is configured to: generate an operation signal for the driver, calculate a relative rotation state between the main body and the endoscope around a longitudinal axis of the endoscope, generate a correction operation signal by correcting the operation signal according to the relative rotation state, and transmit the correction operation signal to the driver to operate the driver.

20 Claims, 8 Drawing Sheets

(56) References Cited

U.S. PATENT DOCUMENTS

2017/0143191 A1* 5/2017 Haraguchi ......... A61B 1/00154
2017/0157361 A1* 6/2017 Barrish ............ A61B 17/00234

FOREIGN PATENT DOCUMENTS

| JP | 2007-521907 A | 8/2007 |
| JP | 2010-22762 A | 2/2010 |
| JP | 2014-188080 A | 10/2014 |
| WO | 2005/074377 A2 | 8/2005 |
| WO | 2007/052354 A1 | 5/2007 |
| WO | 2016/136613 A1 | 9/2016 |

* cited by examiner

OVERTUBE SYSTEM AND OPERATION METHOD OF THE SAME

TECHNICAL FIELD

The present invention relates to an overtube system and an operation method of using an overtube system.

This application is a continuation application based on a PCT International Application No. PCT/JP2018/021991, filed on Jun. 8, 2018. The content of the POT International Application is incorporated herein by reference.

BACKGROUND ART

An endoscope is widely utilized for observing and performing treatment on a lesion portion in gastrointestinal tract.

It is desired to achieve a stable visual field image capturing the lesion portion when a distal end portion of the endoscope approaches to the vicinity of the lesion portion.

In Japanese Unexamined Patent Application, First Publication No. 2014-188080, an overtube configured for introducing an endoscope and having a balloon for fixation is disclosed. The distal end portion of the overtube can be temporarily fixed to a desired position in the gastrointestinal tract by inflating the balloon inside the gastrointestinal tract. As a result, a position of the distal end portion of the endoscope inserting through the overtube is stabilized.

SUMMARY

According to a first aspect of the present disclosure, an overtube system configured to introduce an endoscope into a body, includes a tubular main body formed to be insertable for the endoscope; a balloon attached to an outer circumferential surface of the main body; a driver configured to inflate and deflate the balloon; and a controller configured to control the driver. The controller is configured to generate an operation signal for the driver, calculate a relative rotation state between the main body and the endoscope around a longitudinal axis of the endoscope, generate a correction operation signal by correcting the operation signal according to the relative rotation state, and transmit the correction operation signal to the driver to operate the driver.

According to a second aspect of the present disclosure, in the overtube system according to the first aspect, the controller may be configured so receive an endoscopic image from the endoscope and calculate the relative rotation state according to the endoscopic image.

According to a third aspect of the present disclosure, in the overtube system according to the second aspect, the controller may be configured to receive a first image from the endoscope, generate the operation signal to make the balloon to perform a predetermined operation, transmit the operation signal so the driver so as to make the balloon realize the predetermined operation, receive a second image obtained by the endoscope after the predetermined operation, and calculate the relative rotation state according to the first image and the second image.

According to a fourth aspect of the present disclosure, in the overtube system according to the first aspect, the controller may be configured to extract a first characteristic point from the first image, extract a second characteristic point corresponding to the first characteristic point from the second image, and indicate a vector from the first characteristic point toward the second characteristic point by superimposing the first image and the second image so as to calculate the relative rotation state.

According to a fifth aspect of the present disclosure, the overtube system according to the first aspect may further include an operator configured to transmit an output to the controller, and the controller may be configured to generate the operation signal according to the output.

According to a sixth aspect of the present disclosure, the overtube system according to the fifth aspect may further include a plurality of balloons attached to the outer circumferential surface of the main body; and she driver configured to independently inflate and deflate each of the plurality of balloons, and the controller may be configured to determine which balloon corresponding to the output among the plurality of balloons, generate the operational signal for controlling the driver to inflate and deflate the balloon corresponding to the output according to the output, and generate the correction operation signal by correcting a setting of the balloon corresponding to the output according to the relative rotation state.

According to a seventh aspect of the present disclosure, in the overture system according to the sixth aspect, the operator may be configured to transmit a direction for moving a visual field of the endoscope as the output to the controller, and the controller may be configured to determine which balloon corresponds to the direction among the plurality of balloons, generate the operation signal for controlling the driver to inflate and deflate the balloon corresponding to the direction according to the direction transmitted from the operator, and generate the correction operation signal by correcting a setting of the balloon corresponding to the direction according to the relative rotation state.

According to an eighth aspect of the present disclosure, in the overtube system according to the seventh aspect, the controller may be configured to generate the correction operation signal by correcting the setting of the balloon so as to withdraw the relative rotation between the main body and the endoscope according to the relative rotation state.

According to a ninth aspect of the present disclosure, in the overtube system according to the first aspect, the relative rotation state may be determined by a rotation amount detection sensor provided in the main body.

According to a tenth aspect of the present disclosure, the overtube system according to the first aspect may further include a notification means configured to notify a user of the overtube system of the relative rotation state.

According to an eleventh aspect of the present disclosure, an operation method of an overtube system, the overtube system having a tubular main body formed to be insertable for the endoscope and a balloon attached to an outer circumferential surface of the main body, the balloon being inflated and deflated by a driver, the operation method includes generating an operation signal for the driver; calculating a relative rotation state between the main body and the endoscope around a longitudinal axis of the endoscope; generating a correction operation signal by correcting the operation signal according to the relative rotation state; and transmitting the correction operation signal to the driver to operate the driver.

According to a twelfth aspect of the present disclosure, the operation method of an overtube system according to the eleventh aspect may further include receiving an endoscopic image from the endoscope and calculating the relative rotation state according to the endoscopic image.

According to a thirteenth aspect of the present disclosure, the operation method of an overtube system according to the twelfth aspect may further include when calculating the relative rotation state, receiving a first image from the endoscope; generating the operation signal to make the balloon perform a predetermined operation; transmitting the operation signal Co the driver so as to make the balloon realize the predetermined operation; receiving a second image obtained by the endoscope after the predetermined operation; and calculating the relative rotation state according to the first image and the second image.

According to a fourteenth aspect of the present disclosure, the operation method of an overtube system according to the thirteenth aspect may further include when calculating the relative rotation state, extracting a first characteristic point from the first image; extracting a second characteristic point corresponding to the first characteristic point from the second image; and indicating a vector from the first characteristic point toward the second characteristic point by superimposing the first image and the second image so as to calculate the relative rotation state.

According to a fifteenth aspect of the present disclosure, in the operation method of an overtube system according to the eleventh aspect, the overtube system may further include an operator configured to transmit an output to the controller, and the operation method may further include generating the operation signal according to the output when generating the operation signal.

According to a sixteenth aspect of the present disclosure, in the operation method of an overtube system according to the fifteenth aspect, the overtube system may further include a plurality of balloons attached to the outer circumferential surface of the main body; and the driver configured to independently inflate and deflate each of the plurality of balloons, and the operation method may further include when generating the operation signal, determining which balloon corresponds to the output among the plurality of balloons, and generating the operational signal for controlling the driver to inflate and deflate the balloon corresponding to the output according to the output, and when generating the correction operation signal, generating the correction operation signal by correcting a setting of the balloon corresponding to the output according to the relative rotation state.

According to a seventeenth aspect of the present disclosure, the operation method of an overtube system according to the sixteenth aspect may further include when generating the operation signal, determining which balloon corresponds to the direction among the plurality of balloons, and generating the operation signal for controlling the driver to inflate and deflate the balloon corresponding to the direction according to the direction transmitted from the operator, and when generating the correction operation signal, generating the correction operation signal by correcting a setting of the balloon corresponding to the direction according to the relative rotation state.

According to an eighteenth aspect of the present disclosure, the operation method of an overtube system according to the seventeenth aspect further include when generating the correction operation signal, generating the correction operation signal by correcting the setting of the balloon so as to withdraw the relative rotation between the main body and the endoscope according to the relative rotation state.

According to a nineteenth aspect of the present disclosure, in the operation method of an overtube system according to the eleventh aspect, when calculating the relative rotation state, the relative rotation state may be determined by a rotation amount detection sensor provided in the main body.

According to a twentieth aspect of the present disclosure, the operation method of an overtube system according to the eleventh aspect may further include notifying a user of the overtube system of the relative rotation state.

DESCRIPTION OF EMBODIMENT

A first embodiment of the present disclosure will be described by referring to FIG. 1 to FIG. 7.

Figure 1:
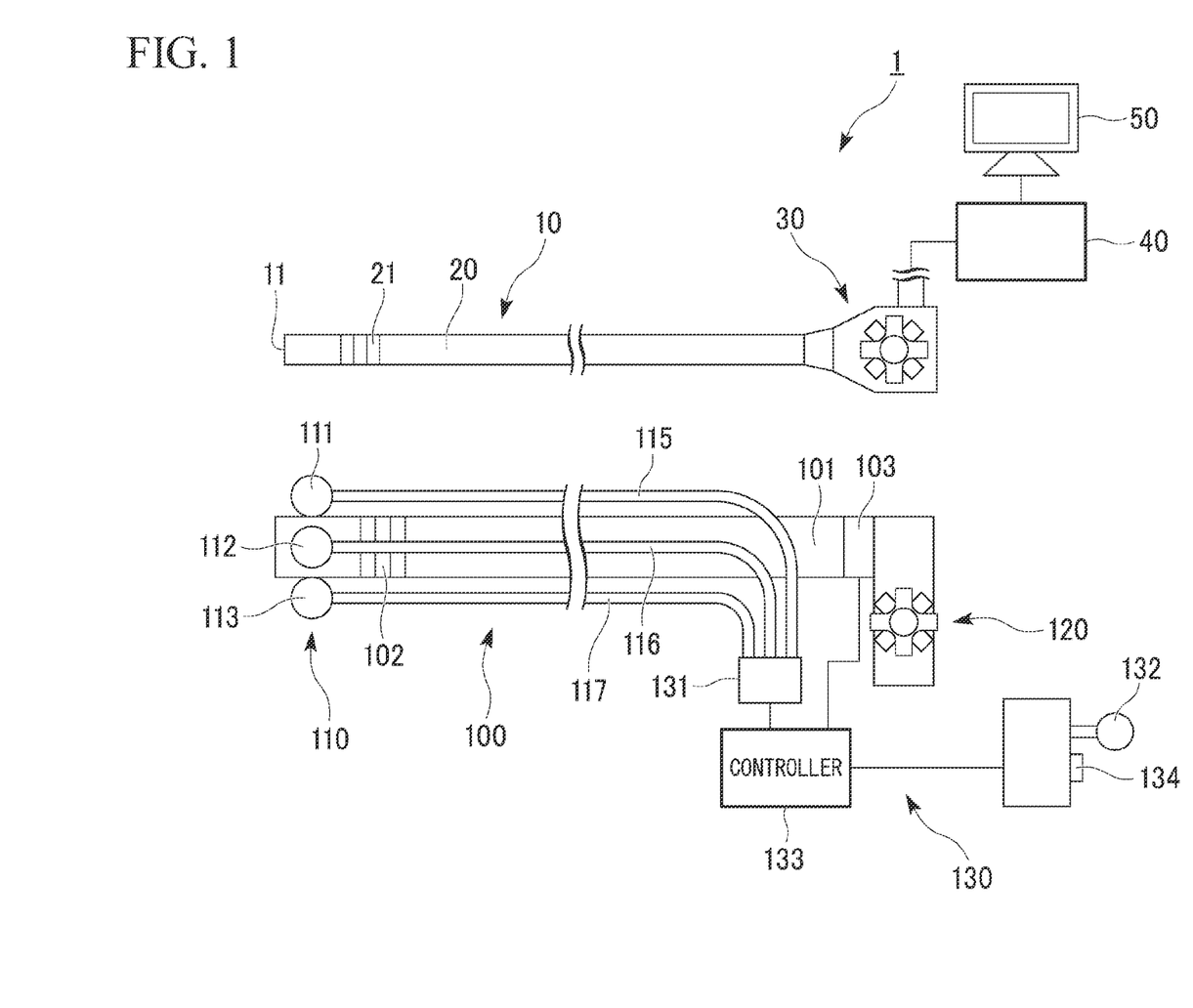
FIG. 1 is a schematic view showing an overall structure of an overtube system according to a first embodiment of the present disclosure.

FIG. 1 is a view showing an overtube system 100 according to the present embodiment and an endoscope 10 as an introducing target.

The endoscope 10 has an elongated flexible insertion portion 20 and an operation portion 30 provided at a proximal end portion of the insertion portion 20. An observation mechanism 11 including an imaging element, an illumination device and the like is attached to a distal end of the insertion portion 20. An image inside a body that is acquired by the observation mechanism 11 is suitably processed in an image processing device 40 and then displayed on a monitor 50.

The insertion portion 20 has a bending portion 21 including a plurality of nodal rings or bending pieces. The plurality of nodal rings and the like of the bending portion 21 are connected with the operation portion 30 via wires and the like such that it is possible to bend the bending portion 21 by operating the operation portion 30. An orientation of the observation mechanism 11 may be changed by bending the bending portion 21.

The configuration of the endoscope 10 described above is publicly well known. Accordingly, a conventional endoscope selected in consideration of a measurement of the insertion portion 20, a bending freedom degree of the bending portion 21 and the like may be utilized as the endoscope 10.

The overtube system 100 has a tubular main body 101, a balloon assembly 110 attached to an outer circumferential surface of she main body 101, a first operation portion 120 attached to a proximal end of the main body 101, and a second operation portion 130 connected to the balloon assembly 110.

The main body 101 has flexibility. An inner diameter of the main body 101 is larger than an outer diameter of the insertion portion 20 of the endoscope 10 such that the insertion portion 20 may be inserted through the inside of the main body 101. The main body 101 has a bending portion 102 having the same mechanism with that of the bending portion 21. The bending portion 102 may be bent to a desired direction by operating the first operation portion 120.

Figure 2:
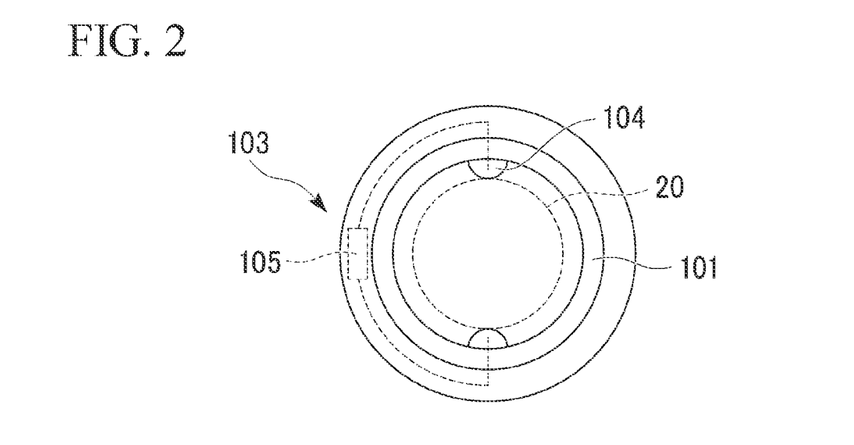
FIG. 2 is a view showing a main body of the overtube system viewed from a proximal end side.

A sensor (relative rotation detection means) 103 is attached so the proximal end portion of the main body 101 FIG. 2 is a view showing the main body 101 from the proximal end side. The sensor 103 has a track ball 104 disposed in an internal cavity of the proximal end portion of the main body 101, and an encoder 105 configured to detect a rotation amount of the track ball 104. The track ball 104 is configured to come in contact with an external surface of the insertion portion 20 that is inserted through the main body 101, and when the insertion portion 20 rotates with respect to the main body 101 around an axis of the main body 101, the track ball 104 also rotates. Accordingly, the sensor 103 outputs a relative rotation amount (relative rotation state) of the insertion portion 20 with respect to the main body 101 as a detection value of the encoder 105.

Figure 3:
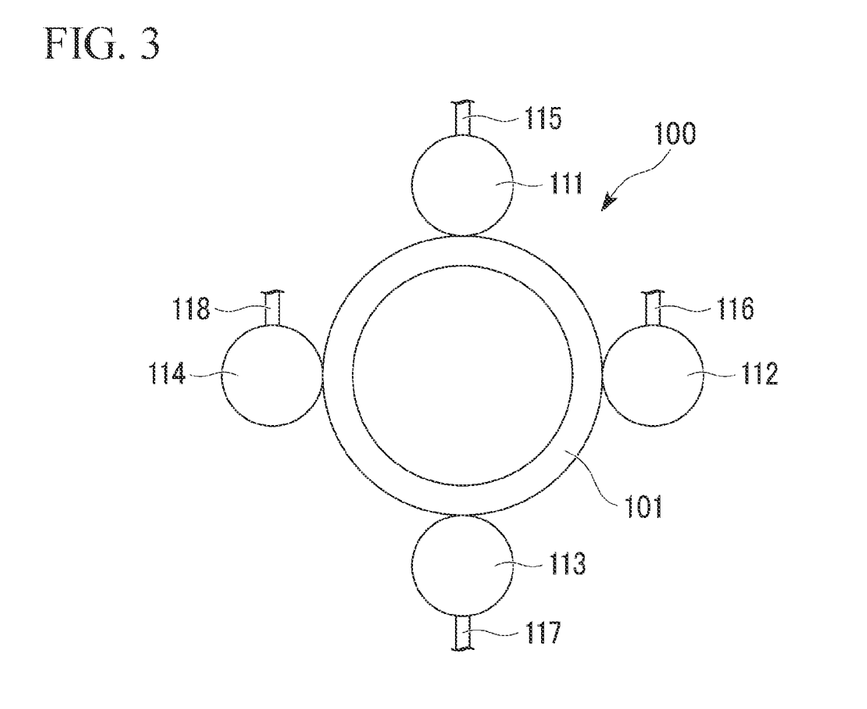
FIG. 3 is a view showing the main body viewed from a distal end side.

FIG. 3 is a view showing the main body 101 from the distal end side. The balloon assembly 110 has four balloons 111, 112, 113, 114. Each balloon is fixed to the external circumferential surface between the distal end of the main body 101 and the bending portion 102. Fixation positions of the four balloons are separated from each other such that two fixation positions of adjacent balloons form an angle around the axis of the main body 101 at 90 degrees. Each balloon 111, 112, 113, 114 is connected with a tube 115, 116, 117, 118 configured to supply and recover the fluid, respectively. Each tube 115, 116, 117, 118 extends to the second operation portion 130 along the main body 101.

The second operation portion 130 has a fluid supply portion (driving portion, driver) 131 connected to each tube 115, 116, 117, 118, a stick (operation portion) 132 and a switch 134 provided as a target of an input by a user, and a control portion (controller) 133 connected to the fluid supply portion 131, the stick 132, and the switch 134.

The fluid supply portion 131 has at least a group elements for each balloon, and the group elements are consisted by a fluid source, a driving mechanism, and a flow rate sensor. An example of the fluid source may be a tank or the like. An example of the driving mechanism may be a pump or the like, and the driving mechanism is configured to move the fluid between the fluid source and the balloon. The flow rate sensor is configured to determine a movement amount of the fluid for each balloon. According to the configuration of the fluid supply portion 131, each balloon 111, 112, 113, 114 may be independently inflated and deflated.

Examples of the fluid supplied to the balloon may be gas such as air, carbon dioxide and the like, or liquid such as water, physiologic saline and the like.

The stick 132 is configured to generate an output when the stick is tilted so a desired direction by applying a force. When the force is withdrawn, the stick 132 returns to a state before being tilted and stops the output.

The switch 134 may be set to either state of ON, OFF, and neutral, and may generate an output in either state.

The control portion (controller) 133 is configured to generate an operation signal for controlling the fluid supply portion 131 according to the output from the stick 132 and the switch 134, and the control portion 133 transmits the operation signal to the fluid supply portion 131. Furthermore, the control portion 133 controls the operation of the fluid supply portion 131 in response to an output from the flow rate sensor. The control portion 133 is configured from at least one processor, memory and the like.

Operations of using the overtube system 100 according to the present embodiment will be described below.

A user inserts the insertion portion 20 of the endoscope 10 into the main body 101 from the proximal end of the main body 101, and protrudes the observation mechanism 11 from the main body 101. At this time, in a circumferential direction of the main body 101, a phase of the endoscope 10 in an upward direction, i.e. an upward side in the visual field image of the endoscope 10 is coincided with a phase of the balloon 111 in advance. The switch 134 is set to OFF. In such an state, the user inserts the endoscope 10 and the main body 101 into the body of a patient from the mouth, the anus, and the like, and then moves the observation mechanism 11 to the vicinity of a tissue as an observation target (target tissue). If necessary, the user operates the bending portion 21 and the bending portion 102 to bend the endoscope 10 and the main body 101 respectively.

Figure 4:
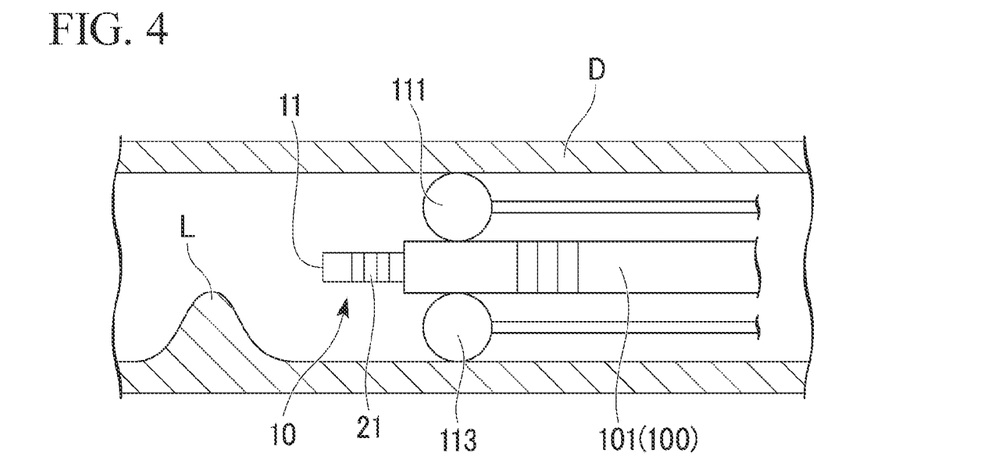
FIG. 4 is a view showing a state in which the main body is temporarily fixed on the gastrointestinal tract.

When the observation mechanism 11 reaches the target tissue, the user determines a position for temporarily fixing, the main body 101 while viewing the target tissue displayed on the monitor, and set the switch 134 to ON. The control portion receives the ON output from the switch 134 so as to generate the operation signal according to the ON output and transmits the operation signal to the fluid supply portion 131. The fluid supply portion 131 receiving the operation signal supplies the flu d to all of the balloons in the same condition. As a result, each balloon 111, 112, 113, 114 is inflated uniformly. When the user sets the switch 134 to neutral, the control portion 133 generates the operation signal according to the neutral output, and the control portion 133 transmits the operation signal to the fluid supply portion 131. As a result, the fluid supply to each balloon 111, 112, 113, 114 is stopped and the inflated state is maintained. Accordingly, after setting the switch 134 to ON to inflate each balloon 111, 112, 113, 114 to a suitable size, by setting the switch 134 to neutral, it is possible to make each balloon 111, 112 (not shown), 113, 114 (not shown) come in contact with the wall of the gastrointestinal tract so as to temporarily fix the main body 101 to the gastrointestinal tract D.

After temporarily fix the main body 101 to the gastrointestinal tract, the user may protrude the bending portion 21 of the endoscope 10 from the main body 101 to observe the target tissue L. It is possible to change a position of the target tissue L in the visual field of the endoscope 10 or similar state by suitably bending the bending portion 21.

The user may desire changing a view point which cannot be realized by only operating the bending portion 21. However, the distal end portion of the main body 101 is fixed to the gastrointestinal tract D by the balloon 111-114, thus bending the bending portion 102 will not change the view point.

In this case, the user operates the second operation portion 130 to change the fixation position of the endoscope 10 in the gastrointestinal tract P while keeping the temporally fixation state of the main body 101.

Figure 5:
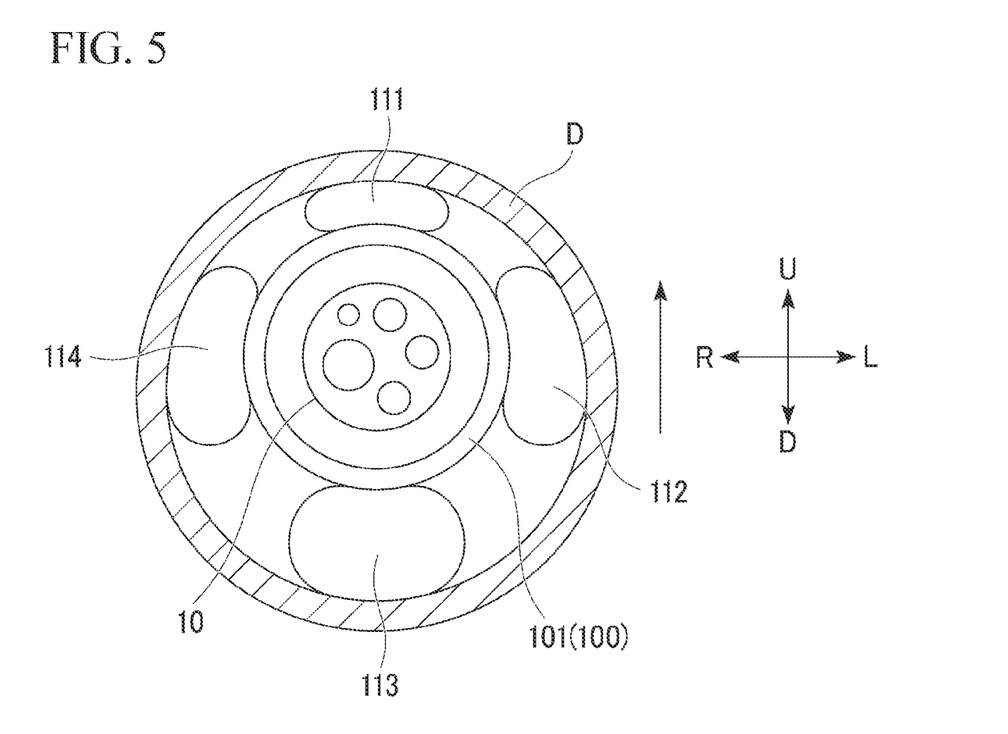
FIG. 5 is a view showing a state in which the main body moves inside the gastrointestinal tract.

For example, in a case in which the user desires to observe the target tissue from a higher position, the user tilts the stick 132 to the upper side. The control portion 133 receiving the output generates the operation signal and transmits the operation signal to the fluid supply portion 131. The fluid supply portion 131 receiving the operation signal further supplies the fluid to the balloon 113 disposed at the downward side of the endoscope 10 so as to inflate the balloon 113, while recovering the fluid in the balloon 111 disposed at the upward side of the endoscope 10 so as deflate the balloon 111. As a result, as shown in FIG. 5, the main body 101 moves toward the upward direction (direction U in FIG. 5) of the endoscope 10 in the gastrointestinal tract D while maintaining the temporally fixation state. In other words, the position of the endoscope 10 protruding from the main body 101 moves upward in the visual field of the endoscope 10 in the gastrointestinal tract D such that it is possible to observe the target tissue L from a higher position in a bird's-eye view.

The control portion 133 inflates at least one of the balloon 111-114 and deflates at least another one according to the output from the stick 132. For example, when the stick 132 is tilted right downward, the control portion 133 generates the operation signal to inflate the balloons 111, 112 disposed in the upward side and the left side of the endoscope 10, and to deflate the balloons 113, 114 disposed in she downward side and the right side thereof. The left side and the right side described above is defined with reference to the state of vi ng the endoscope 10 from the proximal end side toward the distal end side.

The user may dynamically change the view point in the visual field of the endoscope 10 by combining the operations of the bending portion 21 and the operations of the balloons 111-114.

When the endoscope 10 and the main body 101 advances in the meandering gastrointestinal tract and the bending portion 21 is protruded from the main body 101 there is a case in which the insertion portion 20 unintentionally rotates with respect to the main body 101 around the axis of the main body 101. When the insertion portion 20 and the main body 101 rotate relatively with each other, there is a discrepancy occurring in the correspondence between the upward-downward direction and the left-right direction of the endoscope 10 and the configurations of the balloons 111-114. The operation signal of the control portion 133 described above is generated by taking the initial state as a reference, wherein the upward-downward direction and the left-right direction of the endoscope 10 and the configurations of the balloons 111-114 correspond to each other in the initial state, therefore if the stick 132 is operated when she insertion portion 20 and the main body 101 is not in the initial state, the overtube system 100 moves in a direction different from the direction according to the intention of the user. As a result, it is complicated to move the overtube system 100 in a desired direction.

According to the overtube system 100 according to the present embodiment, the control portion 133 performs correction to withdraw the relative rotation and generates the operation signal according to the state of the relative rotation of the insertion portion 20 and the main body 101. Details will be described below.

Figure 6:
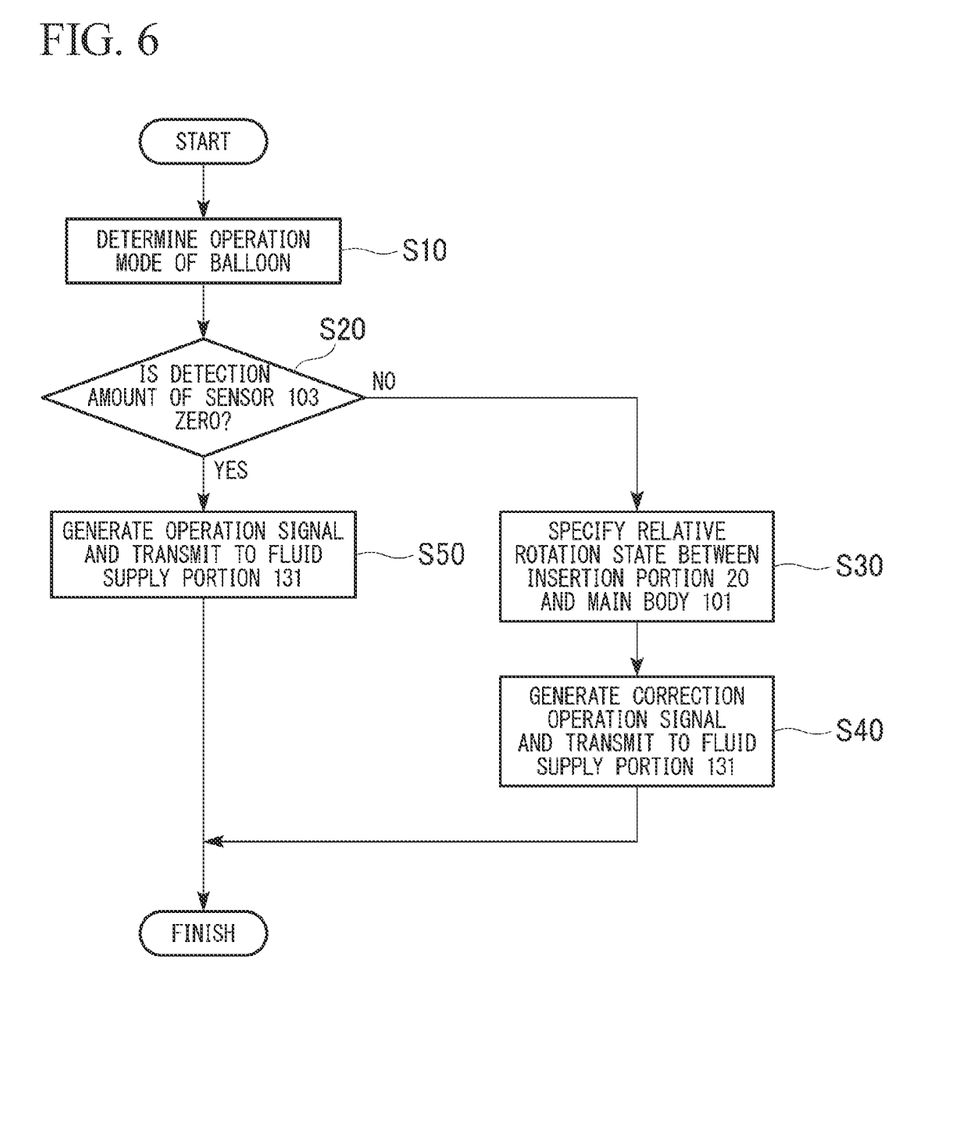
FIG. 6 is a flow chart showing an operation flow of a controller after receiving an output of a stick.

FIG. 6 is a flow chart showing an operation flow of the control portion 133 after receiving the output of the stick 132.

During Step S10, the control portion 133 determines an operation mode of the balloon according to the output of the stick 132, wherein the operation mode of the balloon includes information such as the balloons to be inflated, the balloons to be deflated, the inflation amount, and the deflation amount. The determination may be made by calculating according to mathematical expressions given to the control portion 133 in advance, or the determination may be made by referring to a table given to the control portion 133 in advance.

Subsequently in Step S20, the control portion 133 acquires a detection amount of the sensor 103 and determines whether the detection amount is zero.

In Step S20, if the determination result is "Yes", the process proceeds to Step S50. In this case, since it is not necessary to perform correction with respect to the operation signal, the control portion 133 generates the operation signal corresponding to the output of the stick 132 and then transmits the operation signal so the fluid supply portion 131, and the process is finished.

The generation of the operation signal during Step S50 is performed after the determination during Step S20. Accordingly, the operation signal generated in Step S50 may be considered to be corrected by considering the relative rotation state between the insertion portion 20 and the main body 101, and the correction amount is zero.

In Step S20, if the determination result is "No", the process proceeds to Step S30. During Step S30, the control portion 133 specifies the relative rotation state between the insertion portion 20 and the main body 101 according to the detection amount of the sensor 103.

Subsequently in Step S40, the control portion 133 generates the operation signal corresponding to the output of the stick 132. Furthermore, the control portion 133 performs correction with respect to the generated operation signal according to the specified relative rotation state in Step S30 so as to generate a correction operation signal. The calculation of the correction amount may be made by performed according to mathematical expressions given to the control portion 133 in advance, or by referring to a table given to the control portion 133 in advance. The control portion 133 transmits the generated correction operation signal to the fluid supply portion 131, and the process is finished.

Figure 7:
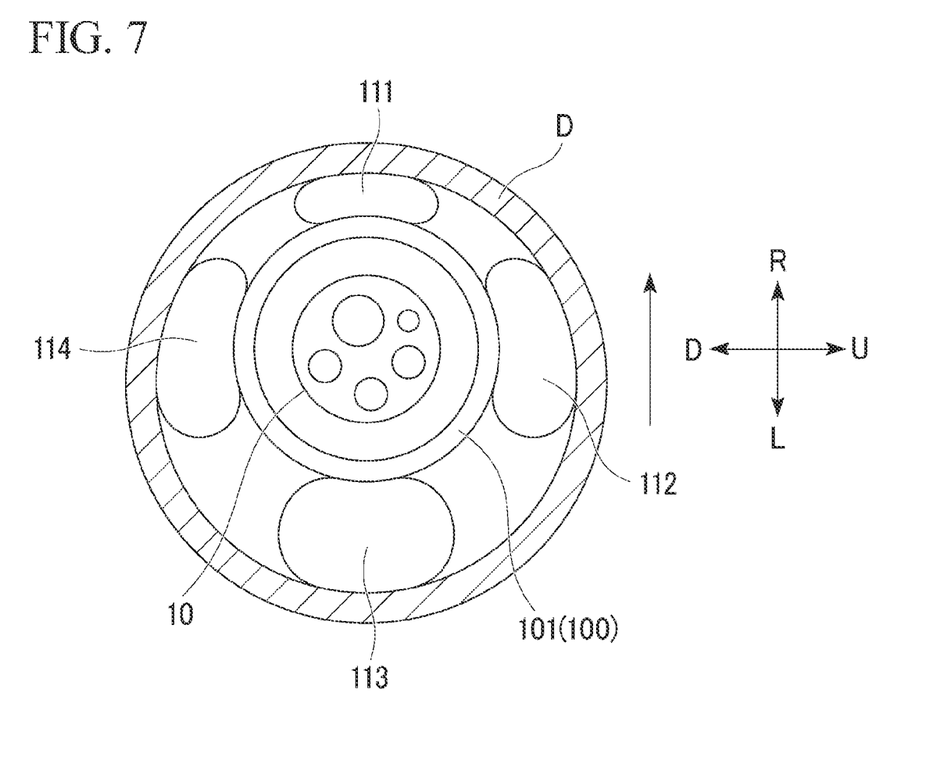
FIG. 7 is a view showing an example of an operation of the main body when the main body and an insertion portion are relatively rotated from an initial state.

As an example, as shown in FIG. 7, a case in which viewed from the distal end side of the main body 101, the insertion portion 20 rotates clockwise by 90 degrees from the initial state is considered. If the user attempts to move the main body 101 upward of the visual field of the endoscope 10, without any correction, as a result of inflating the balloon 113 while deflating the balloon 111, the main body 101 moves toward the right side of the visual field of the endoscope 10 (direction R in FIG. 7).

In Step S30, when the control portion 133 according to the present embodiment specifies that the insertion portion 20 has rotated clockwise by 90 degrees from the initial state, the control portion 133 corrects the operation signal generated according to the output of the stick 132 in Step S40 to generate the correction operation signal for causing the balloon 114 to be inflated and the balloon 112 to be deflated. As a result, the main body 101 moves upward in the visual filed of the endoscope 10 following the intention of the user. In other words, according to the correction operation signal, the effect of the above-described relative rotation is withdrawn. Accordingly, the fluid supply portion 131 driven by the correction operation signal inflates at least one of the balloons 111-114 and deflates at least another one of the balloons 111-114 so as to move the distal end portion of the main body 101 toward a direction corresponding to the direction toward which the stick 132 is tilted by the user.

Accordingly, the user may always move the main body 101 in the desired direction in die visual field of the endoscope 10 by tilting the stick 132 in the direction to which the user desires the main body 101 to be moved in the visual field of the endoscope 10. Accordingly, the user does not need to pay attention to the relative rotation state between the insertion portion 20 and the main body 101 such that the operations become intuitive and simple.

As described above, according to the overtube system 100 according to the present embodiment, it is possible to stabilize the endoscope 10 in the gastrointestinal tract by temporally fixing the main body 101 in the gastrointestinal tract using the balloon 111-114. Furthermore, it is possible to observe the lesion from various view points by combining the operations of the bending portion 20 and the balloons 111-114.

With respect to the overtube system according to the present embodiment, various modifications may be applied. A plurality of modifications will be described below, however other modifications may be possible. Two or more modifications may be suitably combined.

Instead of the sensor 103 configured in a track ball style as the means for detecting the relative rotation state between the insertion portion and the main body 101, an optical sensor configured to read markers provided at a predetermined interval therebetween on the outer circumferential surface of the insertion portion may be utilized.

The sensor 103 may be disposed in an intermediate portion in the longitudinal direction of the main body 101, or a position close to the distal end.

The positional relationship between the balloon and the endoscope in the initial state may be suitably determined. For example, in the initial state, the positions of the balloons may not be coincide with the upward direction, downward direction, left direction, and the right direction.

The tubes 115-118 may be provided along the main body 101 by being bundled using a binding band or the like. Conduit lines having she same functions with the tubes 115-118 may be provided inside the wall of the main body 101.

The correction according to the relative rotation state may be performed in a non-step manner, or performed by a predetermined correction amount such as 5 degrees, for example. It is possible to operate the overtube more intuitively by performing the correction in the non-step manner.

Instead of performing correction to the operation signal generated according to the output of the stick 132 to generate the correction operation signal, it is possible to directly generate the correction operation signal according to the output of the stick 132 and the relative rotation amount.

Other interface may be utilized instead of the stick 132. Examples of other interface may be cross direction buttons corresponding to the upward direction, downward direction, left direction, and right direction, and virtual keys corresponding to upward direction, downward direction, left direction, and right direction and the like displayed on the monitor 50.

The stick 132, the switch 134 and the like may be configured to be attachable to the operation portion 30 of the endoscope 10. In this case, the user may operate the overtube system 100 without separating hand from the endoscope 10 so as to improve operability.

The overtube system 100 may not have the bending portion 102 and the first operation portion 120. In the case, the endoscope 10 and the main body 101 can be bent together by driving the bending portion 21 of the endoscope 10 in the main body 101.

A second embodiment of the present disclosure will be described by referring to FIG. 8 and FIG. 9. In the description below, common configurations described above will be designated with the same reference signs and reductant description will be omitted.

Figure 8:
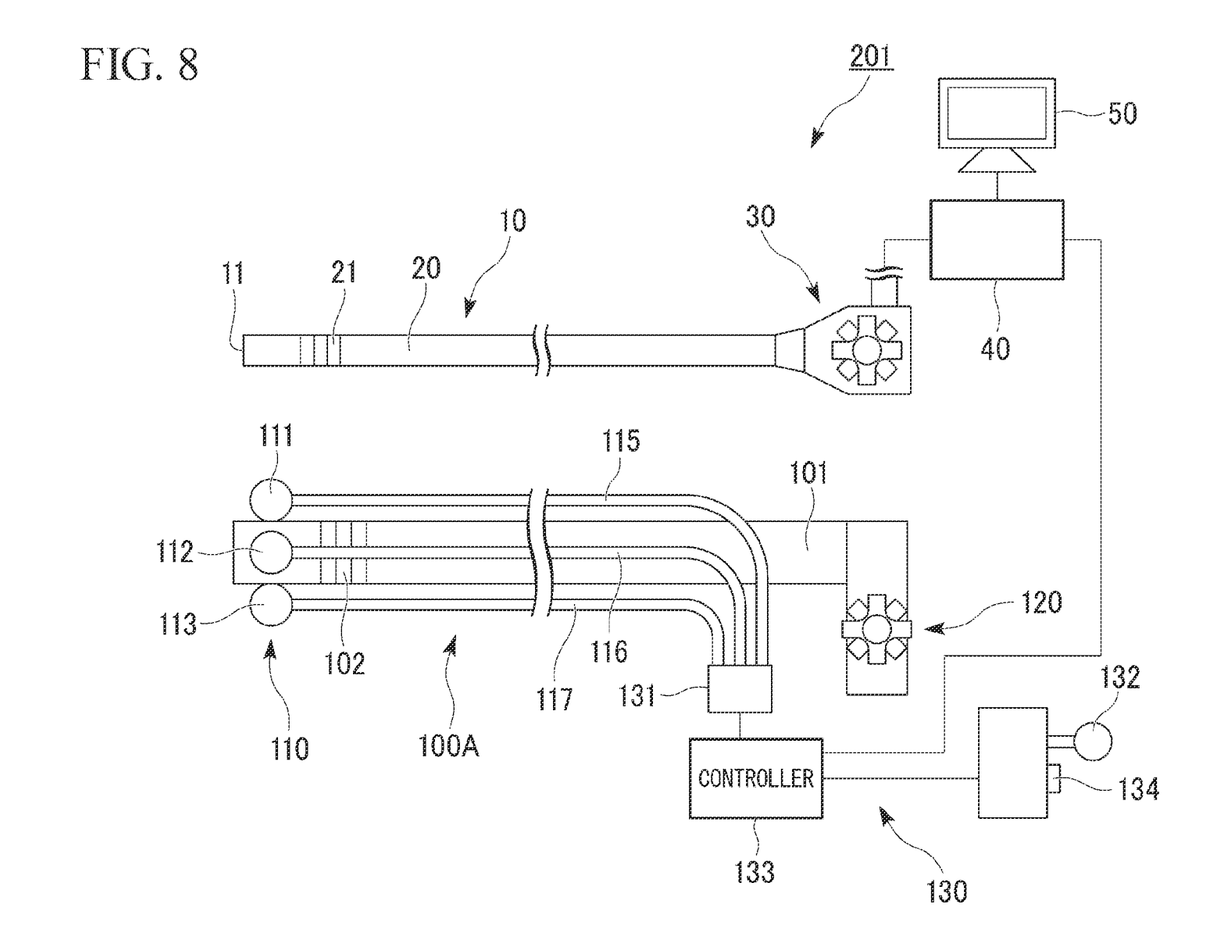
FIG. 8 is a schematic view showing an overall structure of an overtube system, according to a second embodiment of the present disclosure.
Figure 9:
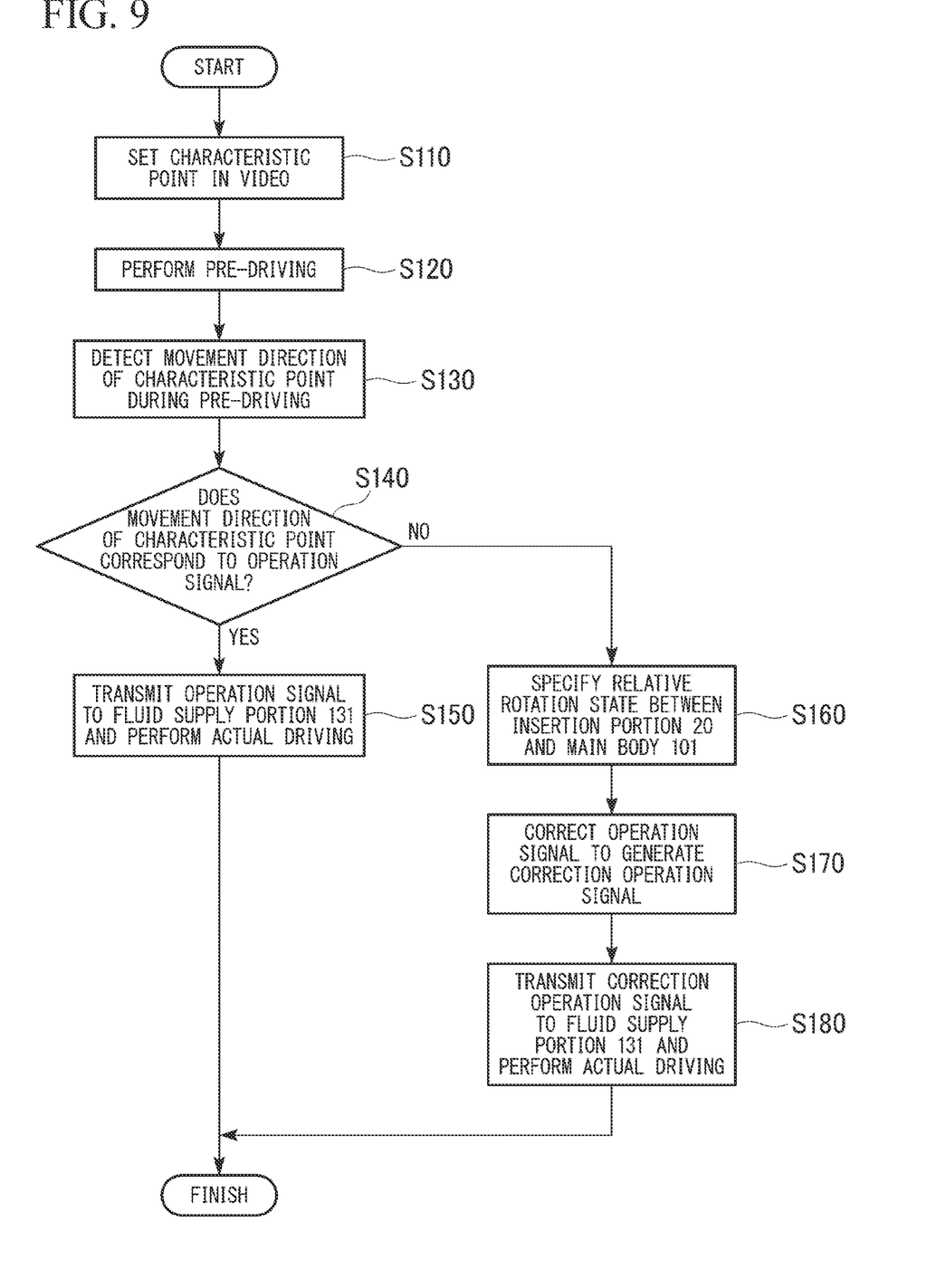
FIG. 9 is a flow chart showing an operation flow of a controller after receiving an output of a stick in the overtube system.

FIG. 8 is a view showing an overtube system 100A according to the present embodiment and the endoscope 10.

In the overtube system 100A, the sensor 103 is not attached to the main body 101. The control portion 133 of the second operation portion 130 is connected to the image processing device 40 of the endoscope 10 such that the control portion 133 may acquire the image displayed on the monitor 50.

Other configurations of the over system 100A are same with the overtube system 100 according to the first embodiment.

Operations of she overtube system 100A will be described. FIG. 9 is a flow chart showing an operation flow of the control portion 133 after receiving an output of the stick 132 in the overtube system 100A.

In Step S110, the control portion 133 receiving the output from the stick 132 acquires an image (a first image) acquired by the observation mechanism 11 and displayed on the monitor 50 at this time from the image processing device 40, and the control portion 133 sets a characteristic point (a first characteristic point) in the first image. Extraction of the first characteristic point may be performed using common known image processing technology. The first characteristic point may be in the target tissue and may be a tissue not being the target tissue.

According to the present embodiment, the image processing device 40 and the control portion 133 are described as different configurations, however, at least one processor and memory configuring the control portion 133 may be configured to function as the image processing device 40. The image processing device 40 may be configured by at least one processor and memory different from that of the control portion 133.

In Step S120, the control portion 133 generates the operation signal according to the output of the stick 132 and transmits the generated operation signal to the fluid supply portion 131 to perform a pre-driving process for driving at least one of the balloons 111-114. The pre-driving process is a driving process (a predetermined operation) for determining whether a change of the positional relationship around the axis between the insertion portion 20 and the main body 101 occurs from the initial state, and the pre-driving process is performed during a short period such as several tens of milliseconds. In other words, the pre-driving process is a driving process for determining whether a discrepancy in the positional relationship around the axis between the insertion portion 20 and the main body 101 occurs.

In Step S130, the control portion 133 acquires an image (a second image) that is displayed on the monitor 50 after the pre-driving process from the image processing device 40, and the control portion 133 detects a characteristic point (a second characteristic point) in the second image corresponding to the first characteristic point. The control portion 133 determines a movement direction of the characteristic point during the pre-driving process according to the positions of the characteristic points between the pre-driving process and after the pre-driving process. Specifically, the control portion 133 identifies a vector from the first characteristic point toward the second characteristic point by superimposing the first image and the second image. In other words, the direction of the identified vector is the movement direction of the characteristic point, and a magnitude of the identified vector is the movement amount. The movement direction of the characteristic point is a parameter showing the movement direction of the main body 101 in the gastrointestinal tract D.

In Step S140, the control portion 133 determines whether the movement of the characteristic point in Step S130 corresponds to the operation signal generates in Step S120.

In a case in which there is no discrepancy between the insertion portion 20 and the main body 101, the movement direction of the characteristic point is in direct opposition with respect to the output of the stick 132 and the movement direction of the characteristic point corresponds to the operation signal. For example, when the stick 132 is tilted to the upward direction, the characteristic point moves downward in the video image of the endoscope 10. In a case in which there is a discrepancy between the insertion portion 20 and the main body 101, the movement direction of the characteristic point is not in direct opposition with respect to the output of the stick 132, thus the movement direction of the characteristic point includes other directional component corresponding to the discrepancy and the movement direction of the characteristic point does not correspond to the operation signal.

In Step S140, if the determination result is Yes, the control portion 133 determines that it is not necessary to perform the correction with respect to the operation signal, and in the continuing Step S150, the control portion 133 transmits the operation signal generated in Step S120 to the fluid supply potion 131 again so as to perform an actual driving process.

In Step S140, if the determination result is No, the control portion 133 determines that it is necessary to perform the correction with respect to the operation signal, and the process proceeds to Step S160. In Step S160, the control portion 133 specifies the relative rotation state between the insertion portion 20 and the main body 101 according to the operation signal generated in Step S120 and the movement direction of the characteristic point detected in Step S130.

In Step S170, the control portion 133 corrects the operation signal generated in Step S120 according to the relative rotation state specified in Step S160 to generate the correction operation signal so as to negate the relative rotation. The calculation of the correction amount necessary for generating the correction operation signal may be performed in the same manner as that according to the first embodiment.

In Step S180, the control signal 133 transmits the correction operation signal generated in Step S170 so the fluid supply portion 131 to perform the actual driving of the balloon.

According to the present embodiment, the control portion 133 functions as the relative rotation detection means instead of the sensor 103. According to the configuration, the same effect with the overtube system 100 according to the first embodiment may be realized.

According to the present embodiment, the pre-driving process is performed at the time of receiving the output of the stick 132; however, the operation mode of the pre-driving process does not have to correspond to the received output of the stick 132. Regardless of the operation direction of the pre-driving process, if only the pre-driving process is performed, the control portion 133 may calculate the relative rotation state according to the acquired first image and the second image. Accordingly, the operation direction of the pre-driving process is not particularly limited. For example, the pre-driving process may be an operation of moving toward a constant predetermined direction regardless of the output of the stick 132.

Several embodiments and modification examples of the present disclosure have been described above, however, technical scope of the present disclosure is not limited to the embodiment and the application examples. Additions, omissions, substitutions and other changes in the structure are possible without departing from the spirit of the present disclosure.

According to the embodiment described above, the example of the control portion generating the correction operation signal in the case in which the insertion portion of the endoscope and the main body of the overtube relative rotate with each other from the initial state is described. Instead of this example, a configuration of including a notification means configured to transmit various information to the user such that the information whether there is a relative rotation or not and the relative rotation amount is transmitted to the user by using the notification means and the control portion does not generate the correction operation signal may be adopted. For example, a specific method of the notification may be displaying on the monitor 50, or using sound notification.

In the case of adopting the configuration, the operations by the user may become somehow complicated, however, the user may suitably change the operation direction of the stick 132 and the like according to the notified content by the notification means so as to move the main body toward the desired direction.

Figure 10:
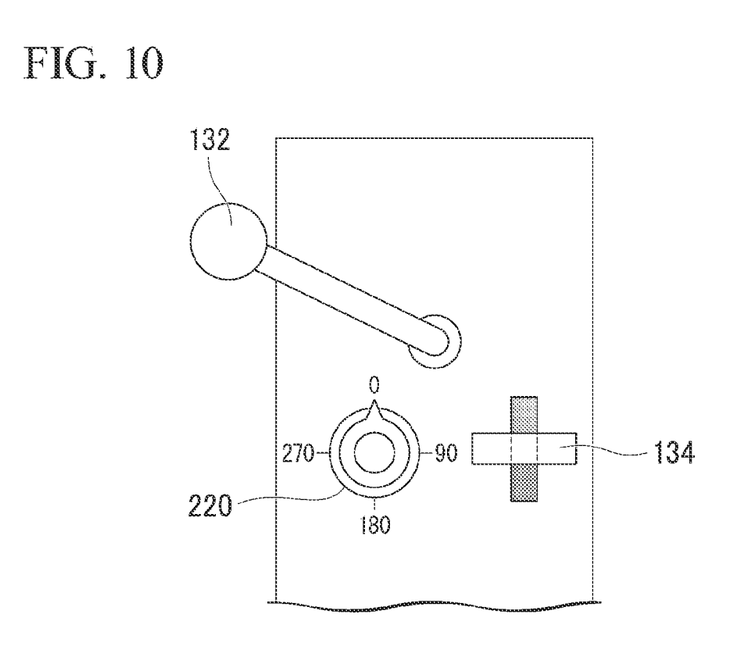
FIG. 10 is a view showing part of a second operation portion according to a modification example.

In order to simply the operation of the user while adopting the configuration, as shown in FIG. 10, a correction dial (a sub interface) 220 may be provided in an user interface of the second operation portion. An encoder (not shown) configured to detect the rotation amount is attached to the correction dial 220, and the encoder is connected with the control portion 133.

In a case in which the correction dial 220 is rotated, the control portion 133 corrects the corresponding relationship between the direction in which the stick 132 is tilted and the driving mode of each balloon 111-114, in other words, regarding which balloon is inflated and which balloon is deflated according to the rotation amount of the correction dial 220. The control portion 133 generates the operation signal corresponding to the output of the stick 132 according to the changed corresponding relationship. Accordingly, the control portion 133 does not correct the generated operation signal and instead, the control portion 133 generates the operation signal in which the relative rotation has been withdrawn.

Accordingly, it is possible to continue making the operation of the main body by the user simple and intuitive by including information for encouraging the user to operate the correction dial 220 before the operation to the stick 132 in addition to the information regarding the rotation amount of the correction dial 220 (how many degrees in clockwise direction or counter-clockwise direction) in the notification information, wherein the in regarding the rotation amount of the correction dial 220 indicates the necessary corresponding relationship information for withdrawing the relative rotation between the insertion portion 20 and the main body 101.

Several embodiments and modification examples of the present disclosure have been described above, however, technical scope of the present disclosure is not limited to the embodiment and the application examples. Additions, omissions, substitutions and other changes in the structure are possible without departing from the spirit of the present disclosure. The present disclosure is not limited to the above-described embodiments and is limited only by the accompanying claims.

What is claimed is:

1. An overtube system configured to introduce an endoscope into a body, comprising:
   a tubular main body formed to be insertable for the endoscope;

a balloon attached to an outer circumferential surface of the main body;
a driver configured to inflate and deflate the balloon; and
a controller configured to control the driver,
wherein the controller is configured to:
generate an operation signal for the driver,
calculate a relative rotation state between the main body and the endoscope around a longitudinal axis of the endoscope,
generate a correction operation signal by correcting the operation signal according to the relative rotation state, and
transmit the correction operation signal to the driver to operate the driver.

2. The overtube system according to claim 1, wherein the controller is configured to receive an endoscopic image from the endoscope and calculate the relative rotation state according to the endoscopic image.

3. The overtube system according to claim 2, wherein the controller is configured to:
receive a first image from the endoscope,
generate the operation signal to make the balloon perform a predetermined operation,
transmit the operation signal to the driver so as to make the balloon realize the predetermined operation,
receive a second image obtained by the endoscope after the predetermined operation, and
calculate the relative rotation state according to the first image and the second image.

4. The overtube system according to claim 1, wherein the controller is configured to:
extract a first characteristic point from the first image,
extract a second characteristic point corresponding to the first characteristic point from the second image, and
indicate a vector from the first characteristic point toward the second characteristic point by superimposing the first image and the second image so as to calculate the relative rotation state.

5. The overtube system according to claim 1, further comprising an operator configured to transmit an output to the controller, wherein the controller is configured to generate the operation signal according to the output.

6. The overtube system according to claim 5, further comprising:
a plurality of balloons attached to the outer circumferential surface of the main body; and
the driver configured to independently inflate and deflate each of the plurality of balloons,
wherein the controller is configured to:
determine which balloon corresponds to the output among the plurality of balloons,
generate the operational signal for controlling the driver to inflate and deflate the balloon corresponding to the output according to the output, and
generate the correction operation signal by correcting a setting of the balloon corresponding to the output according to the relative rotation state.

7. The overtube system according to claim 6,
wherein the operator is configured to transmit a direction for moving a visual field of the endoscope as the output to the controller, and
wherein the controller is configured to:
determine which balloon corresponds to the direction among the plurality of balloons,
generate the operation signal for controlling the driver to inflate and deflate the balloon corresponding to the direction according to the direction transmitted from the operator, and
generate the correction operation signal by correcting a setting of the balloon corresponding to the direction according to the relative rotation state.

8. The overtube system according to claim 7, wherein the controller is configured to generate the correction operation signal by correcting the setting of the balloon so as to withdraw the relative rotation between the main body and the endoscope according to the relative rotation state.

9. The overtube system according to claim 1, wherein the relative rotation state is determined by a rotation amount detection sensor provided in the main body.

10. The overtube system according to claim 1, further comprising a notification means configured to notify a user of the overtube system of the relative rotation state.

11. An operation method of an overtube system, the overtube system having a tubular main body formed to be insertable for the endoscope and a balloon attached to an outer circumferential surface of the main body, the balloon being inflated and deflated by a driver, the operation method comprising:
generating an operation signal for the driver;
calculating a relative rotation state between the main body and the endoscope around a longitudinal axis of the endoscope;
generating a correction operation signal by correcting the operation signal according to the relative rotation state; and
transmitting the correction operation signal to the driver to operate the driver.

12. The operation method of an overtube system according to claim 11, further comprising:
receiving an endoscopic image from the endoscope and calculating the relative rotation state according to the endoscopic image.

13. The operation method of an overtube system according to claim 12, further comprising:
when calculating the relative rotation state, receiving a first image from the endoscope;
generating the operation signal to make the balloon perform a predetermined operation;
transmitting the operation signal to the driver so as to make the balloon realize the predetermined operation;
receiving a second image obtained by the endoscope after the predetermined operation; and
calculating the relative rotation state according to the first image and the second image.

14. The operation method of an overtube system according to claim 13, further comprising:
when calculating the relative rotation state, extracting a first characteristic point from the first image;
extracting a second characteristic point corresponding to the first characteristic point from the second image; and
indicating a vector from the first characteristic point toward the second characteristic point by superimposing the first image and the second image so as to calculate the relative rotation state.

15. The operation method of an overtube system according to claim 11,
wherein the overtube system further comprises an operator configured to transmit an output to the controller, and wherein the operation method further comprises generating the operation signal according to the output when generating the operation signal.

16. The operation method of an overtube system according to claim 15,
wherein the overtube system further comprises:
a plurality of balloons attached to the outer circumferential surface of the main body; and
the driver configured to independently inflate and deflate each of the plurality of balloons, and
wherein the operation method further comprises:
when generating the operation signal, determining which balloon corresponds to the output among the plurality of balloons, and generating the operational signal for controlling the driver to inflate and deflate the balloon corresponding to the output according to the output, and
when generating the correction operation signal, generating the correction operation signal by correcting a setting of the balloon corresponding to the output according to the relative rotation state.

17. The operation method of an overtube system according to claim 16, further comprising:
when generating the operation signal, determining which balloon corresponds to the direction among the plurality of balloons, and generating the operation signal for controlling the driver to inflate and deflate the balloon corresponding to the direction according to the direction transmitted from the operator, and
when generating the correction operation signal, generating the correction operation signal by correcting a setting of the balloon corresponding to the direction according to the relative rotation state.

18. The operation method of an overtube system according to claim 17, further comprising: when generating the correction operation signal, generating the correction operation signal by correcting the setting of the balloon so as to withdraw the relative rotation between the main body and the endoscope according to the relative rotation state.

19. The operation method of an overtube system according to claim 11, wherein when calculating the relative rotation state, the relative rotation state is determined by a rotation amount detection sensor provided in the main body.

20. The operation method of an overtube system according to claim 11, further comprising notifying a user of the overtube system of the relative rotation state.

* * * * *